(12) United States Patent
Emarlou

(10) Patent No.: US 9,155,848 B2
(45) Date of Patent: Oct. 13, 2015

(54) METHOD AND SYSTEM FOR VAPORIZATION OF A SUBSTANCE

(75) Inventor: Hamid Emarlou, Los Gatos, CA (US)

(73) Assignee: Vapir, Inc., San Jose, CA (US)

( * ) Notice: Subject to any disclaimer, the term of this patent is extended or adjusted under 35 U.S.C. 154(b) by 1161 days.

(21) Appl. No.: 11/872,040

(22) Filed: Oct. 15, 2007

(65) Prior Publication Data

US 2009/0095287 A1    Apr. 16, 2009

(51) Int. Cl.
*A61M 11/00* (2006.01)
*A61M 11/04* (2006.01)
*A61M 15/06* (2006.01)

(52) U.S. Cl.
CPC ........... *A61M 11/041* (2013.01); *A61M 11/042* (2014.02); *A61M 15/06* (2013.01); *A61M 2205/3368* (2013.01); *A61M 2205/3553* (2013.01); *A61M 2205/3584* (2013.01); *A61M 2205/3592* (2013.01); *A61M 2205/502* (2013.01); *A61M 2205/6018* (2013.01); *A61M 2205/8206* (2013.01)

(58) Field of Classification Search
CPC .............. A61M 16/16; A61M 16/109; A61M 2205/3368; A61M 2205/502; A61M 2205/8206; A61M 11/041; A61M 15/06; A61M 2205/3553; A61M 2205/3584; A61M 2205/3592; A61M 2205/6018; A61M 11/042
USPC ............ 128/203.26, 203.27, 204.17, 202.21; 131/194; 239/136; 392/390, 397; 96/361, 362, 363; 261/DIG. 65
See application file for complete search history.

(56) References Cited

U.S. PATENT DOCUMENTS

| | | | |
|---|---|---|---|
| 5,144,962 A | 9/1992 | Counts et al. | |
| 5,249,586 A | 10/1993 | Morgan | |
| 5,388,574 A | 2/1995 | Ingebrethsen | |
| 6,772,756 B2 | 8/2004 | Shayan | |
| 6,990,978 B2 * | 1/2006 | Shayan | 128/203.27 |
| 7,186,958 B1 * | 3/2007 | Nelson | 219/533 |

* cited by examiner

*Primary Examiner* — Steven Douglas
(74) *Attorney, Agent, or Firm* — Terra Law LLP; Benedict O'Mahoney

(57) ABSTRACT

An apparatus for the vaporization of materials that releases active constituents for inhalation without the creation of harmful byproducts such as carcinogens associated with combustion and inhalation of substances. The apparatus is designed to fit ergonomically within the user's hand. The apparatus uses the user's inhalation process for air flow.

13 Claims, 2 Drawing Sheets

METHOD AND SYSTEM FOR VAPORIZATION OF A SUBSTANCE

BACKGROUND OF THE INVENTION

The present invention generally relates to devices for the inhalation of volatile components of a substance, or more particularly to a sophisticated apparatus for the vaporization of materials that release active constituents for inhalation without the creation of harmful byproducts associated with combustion of materials, which is easy to use and provides accurate temperature control and air flow.

Well known within the art is the use of combustion of substances to enable inhalation of volatile materials contained therein. However, recently the hazards associated with such behavior has become well known and of great concern. This process is known as "smoking" and generally involves oxidation, hydrogenation, cracking, distillation and sublimation. Oxidation, hydrogenation, and cracking result in the formation of chemical compounds not present in the original source material and it is these products not present in the original source material that are generally recognized as the most hazardous aspect of smoking. As such it is desirable to heat a substance such that distillation and sublimation occur without combustion. By eliminating combustion as a heat source, the health risks are minimized while enabling the beneficial properties present in the volatile compounds to be utilized.

Plant matter such as tobacco or other herbal medicines, when smoked are also not properly utilized to maximum efficiency. As much as 95% of the active material can be wasted in order to absorb 5% or less of the same. Also, much of the active ingredients and helpful medicines are destroyed by combustion. Various attempts have been tried to overcome the problems associated with smoking.

U.S. Pat. No. 6,772,756 by Shayan and issued on Aug. 10, 2004 is for a Method and system for vaporization of a substance. It discloses an apparatus for the vaporization of materials that releases active constituents for inhalation without the creation of harmful byproducts such as carcinogens associated with combustion and inhalation of substances. However this invention requires a fan and power for the movement of the air in the inhalation device.

U.S. Pat. No. 5,249,586 issued to Morgan discloses an article in which a replaceable tobacco flavor medium is electrically heated by a set of permanent reusable heaters to evolve inhalable flavors or other components in vapor or aerosol form. Each heater heats only a portion of the available tobacco flavor medium so that a plurality of individual puffs of tobacco flavor substance can be delivered sequentially to the smoker. The tobacco flavor medium preferably contains tobacco materials.

U.S. Pat. No. 5,33,574 issued to Ingebrethsen discloses an aerosol delivery article which provides delivery of aerosol particles of relatively small size without the necessity of exposing the material which is aerosolized to a significant degree of heat or high temperatures. An aerosol forming material is a multi-component material comprising an active ingredient and another ingredient having a relatively low vaporization temperature, and preferably that aerosol forming material is in the form of an emulsion. The aerosol forming material is nebulized so as to provide first stage multi-component aerosol particles of fairly large size. The first stage aerosol particles then are subjected to heat so as to vaporize the other ingredient of that aerosol and cause further dispersion of that first stage aerosol. As such, a second stage aerosol composed of fine particles of active ingredient is provided. The heat used to cause the further dispersion of the first stage aerosol is less than that sufficient to cause vaporization, thermal decomposition or undesirable chemical alteration of the active ingredient.

U.S. Pat. No. 5,144,962 issued to Counts discloses a Flavor Delivery Article Method and Apparatus. The Counts Patent electrically heats a material in order to release the flavor. While the Counts patent represented an advancement within the art, the Counts Patent utilized direct heat between the heating element and the medium to effect heat transfer by conduction. This method is flawed in that it does not provide for the optimum temperature according to the material. Also, the material is embedded in the apparatus. A more sophisticated apparatus that allows for the efficient release of desirable elements of a substance is needed.

When tobacco is smoked, many toxic & carcinogenic substances are produced in the process of attempting to ignite and absorb the active component—nicotine. However, it may be desirable to have an apparatus which does not ignite the tobacco, but rather allows for the delivery of nicotine into the blood stream without the tar and other carcinogenic compounds associated with smoking. Such an apparatus would be a revolutionary breakthrough for those trying to quit smoking. Further, given the hazards associated with secondary smoke, a smokeless device is needed to protect non-smokers.

Also, a device is needed which may be used to deliver drugs such as morphine and other opiates that are currently being delivered intravenously. This may also solve many of the problems associated with heroin addicts, such as needle sharing which can lead to dangerous exposure to various diseases. A device is needed which would allow for the delivery of such drugs safely. Currently, devices such as nebulizers may be used to accomplish this. Such devices are flawed, though, in that they require special mixtures of the drugs that must be made into a fog using ultrasound. The present invention does not require the drugs to be specially formulated, but rather allows for an apparatus which may adjust the delivery mode according to the substance being used.

This may also be desirable to health care professionals who do not want to risk exposure to diseases by way of administering needles to patients who may have unknown diseases. Any place where a clean, easy and efficient means of delivering the active elements of a substance would benefit from the present invention.

Accordingly, there is a need for a clean and easy to use device that allows for the release of the essential active elements of a substance through vaporization using just enough heat and air to release them without burning the substance and without creating the toxic byproducts of combustion and denaturing of the initial source material while effectively and optimally delivering a multitude of active elements of different substances.

SUMMARY OF THE INVENTION

In one aspect of the present invention, an apparatus for releasing volatile components of a substance is disclosed. The apparatus comprises in combination a power means through a DC Power Input, a heater means and a heating chamber which serves as a source material holder which is insertable and removable for holding the substance, a suction means as a person inhaling sufficient to create an air flow, a temperature sensing means, a time and temperature control means, a LCD display, a mouthpiece that serves as a receptacle for receiving a vapor that results from the release of volatile components created by heated air directed from the heater means over the substance and releasing volatile elements, and as an opening for allowing release of the vapor all contained in a Unit Casing. There may also be a window means for viewing the vapor, which may contain a light inside. The temperature sensing means may be a thermocouple or resistance temperature detector (RTD). The heater means may be a Ceramic UF Heater. The airflow may be between 0 and 10 Liters/min. The apparatus may release volatile elements into the ambient air. Also, the time and temperature control means may produce a variable heat according to the specific substance being volatized in said apparatus.

The apparatus may further comprise an information input/output means in communication with the power means that displays the temperature and allows for adjustment of said temperature by controlling suction from the inhaling of a person using the device and heat from the heater means. It should be understood that the information input/output means may be in communication in a multitude of ways including wireless and fiberoptic communication. Information may be manually inputted into the information input/output means which in turn electrically communicates with the power means, heater means to adjust the temperature within said apparatus for a specified time. The time elapsed may be displayed on a display means such as an LCD display means. Also, an information retrieval and delivery means in electrical, optical or wireless communication with said power means may be used. This may be a USB, firewire, ethernet, wireless ethernet, ilink interface, A/V interface, telephone cable interface, parallel interface, fiber optics, and serial interface connected to the apparatus and an information source (e.g. computer). The information retrieval and delivery means may be a disk contained the apparatus, particularly it may be contained within the source material holder. The disk may automatically sense the nature of the material contained within and provide information to the apparatus such as to provide optimal release of volatile elements of the substance. The disk may be a mesh materials holder. The mesh materials holder may further have a substance embedded in it. Also, a pre-formed substance with holes formed to be contained within said source material holder may be contained therein. The temperature provided by the heater means is preferably between 0.degree. C. and 300.degree. C.

According to another embodiment, an apparatus for releasing volatile elements of a substance is disclosed comprising in combination a power means in electrical communication with a heater means, a thermocouple for sensing temperature, an information retrieval and delivery means in electrical communication with the power means, a time and temperature control means that adjusts the heat produced by the heater means and length of time heat is produced, information output means in electrical communication with the power means that displays the temperature and time, a source material holder which is insertable and removable for holding the substance, a venturi tube receptacle, a window means containing at least one light and an opening. The time and temperature control means produces a variable heat according to the specific substance being volatized in the apparatus. The heat provided by the heater means is preferably between 0.degree. C. and 300.degree. C. and the airflow between 0 and 10 Liters/min. aaaadswds According to another embodiment, a system and apparatus is disclosed that allows for the inhalation of the active components of a substance comprising a housing configured and sized to fit in the user's hand during use, a power means that supplies power to a heating means, information retrieval and delivery means, time and temperature control means, information input/output means, a suction means which in the preferred embodiment in the inhalation of the user of the device, wherein the suction means delivers air to create an air stream which combines with heat from the heating means to provide a convection air stream. An air stream is directed over a source material holder which includes a cavity for holding a substance, creating a substance vapor air stream and a receptacle having at least one opening in communication with the source material holder receives the substance vapor air stream. The heater is preferably a Ceramic UF Heater. The apparatus may also release the volatile elements from the opening into the ambient air. Time and temperature control means produces a variable heat according to the specific substance being volatized in the apparatus. There may be a light in the window. Also, as discussed in previous embodiments, the information input/output means may be in electrical communication with the power means and allow for adjustment of the temperature, time and airflow. Information may also be manually entered into said information input/output means which in turn electrically communicates with said power means, heater means and suction means to adjust the temperature within said apparatus for a specified time. The information retrieval and delivery means may be a disk contained within said apparatus which automatically senses the nature of the material. Once the disk senses the nature of the material, it delivers a set of instructions to the apparatus such as to provide an optimal release of volatile elements of the substance. A mesh materials holder contained within said source material holder may be used in order to prevent the inhalation of extraneous particles and to contain the substance. The mesh materials holder may also have a substance embedded in it. According to another embodiment, a preformed substance with holes formed to be contained within the source material holder.

These and other features, aspects and advantages of the present invention will become better understood with reference to the following drawings, description and claims.

DETAILED DESCRIPTION OF THE INVENTION

The following detailed description is of the best currently contemplated modes of carrying out the invention. The description is not to be taken in a limiting sense, but is made merely for the purpose of illustrating the general principles of the invention, since the scope of the invention is best defined by the appended claims.

The present invention generally provides an apparatus for the vaporization of materials that release active constituents for inhalation without the creation of harmful byproducts associated with combustion of materials.

In one aspect of the present invention, an apparatus 10 for releasing volatile components of a substance is disclosed. The apparatus 10 comprises in combination a power means through a DC Power Input 6, a heater means and a heating chamber 3 which serves as a source material holder which is insertable and removable for holding the substance, a suction means as a person inhaling sufficient to create an air flow, a temperature sensing means, a time and temperature control means, a LCD display 5, a mouthpiece 1 that serves as a receptacle for receiving a vapor that results from the release of volatile components created by heated air directed from the heater means over the substance and releasing volatile elements, and as an opening for allowing release of the vapor all contained in a Unit Casing 4.

Figure 1:
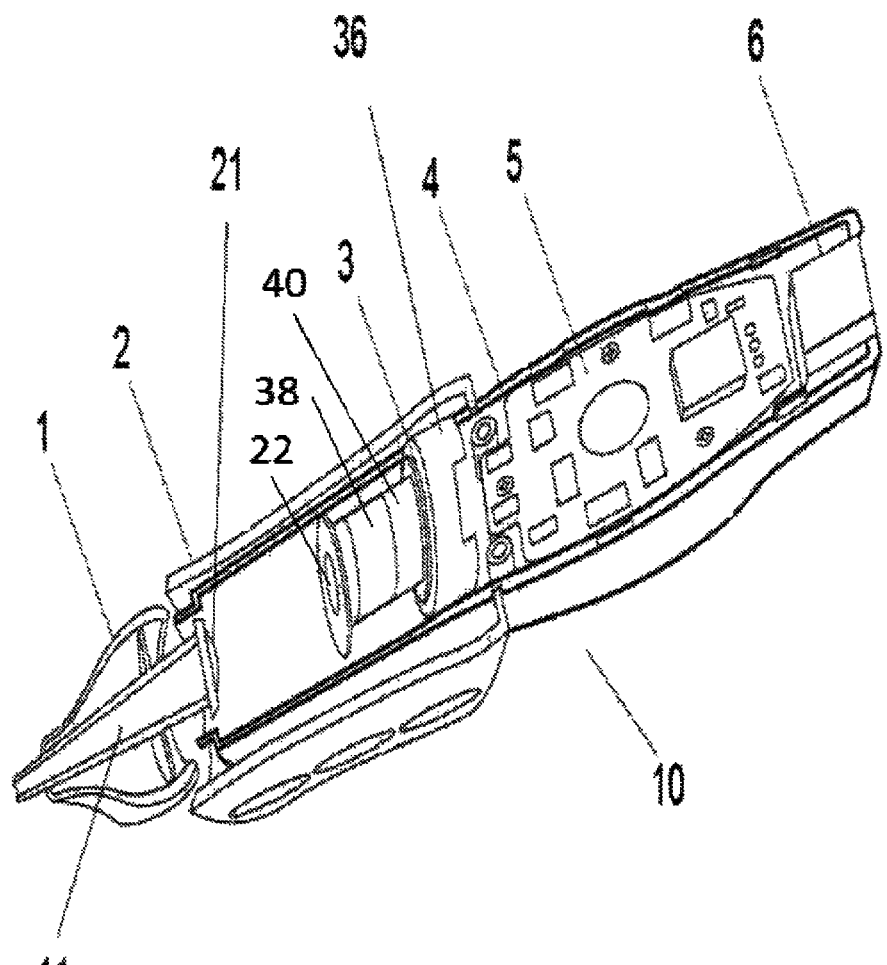
FIG. 1 is an interior cutaway view of the present invention according to a preferred embodiment.
Figure 2:
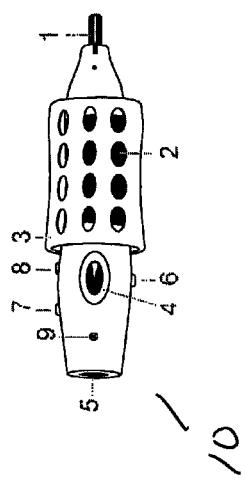
FIG. 2 is a side view of the present invention according to a preferred embodiment.

Referring to FIG. 1 and FIG. 2, shown is a preferred embodiment of the present invention, the apparatus 10 is made of a high heat and impact resistant nylon plastic fiber Unit Casing 4. The apparatus 10 may have a switch means in communication with a power means for turning the apparatus on and off, such as switch. The Switch may have three positions (1) "charge mode" (2) "on mode" and (3) "adaptor mode". When the switch is in (1) charge mode or (3) adaptor mode power from an internal source may not be delivered. The power means is provided in the preferred embodiment through a DC Power Input 6 which is an the end of the apparatus opposite of the mouthpiece 1. In an alternate embodiment, the apparatus 10 may be an internal power source such as standard batteries or lithium ion batteries. Also, the apparatus 10 may utilize a power cord which allows for the power to be supplied by a standard electrical outlet. According to another embodiment, the apparatus 10 may have a rechargeable battery as the power means contained with and a charger stand, wherein the apparatus 10 may be placed and the apparatus 10 allowed to recharge. When the switch is in the "on mode" position, the power means will deliver power.

The device may also have an information delivery and retrieval means in electrical, wireless, or optical communication with the power means. This may be a USB, firewire, ethernet, ilink interface, ANV interface, telephone cable interface, parallel interface, fiber optics, wireless ethernet and/or a serial interface connected to the apparatus and a separate information source (e.g. a personal computer, PDA, etc.). According to one embodiment, a USB cable may be connected to the apparatus 10 and a computer, wherein the computer delivers information to a time and temperature control means. This option may be used by doctors to regulate the dosage of a particular drug to a patient from a remote location or to download a patient's usage data from the device (e.g. how often it was used, at what settings, etc.) A doctor may also monitor and regulate their patients dosage and other aspects of treatment (e.g. airflow, temperature). Also, information may be stored externally, such as on a website for optimal temperatures and settings according to the substance being used. For example, a certain brand of tobacco may have an optimal vaporization program of 122 degrees for the first 2 minutes, the 100 degrees for the next 1 minute then 134 for the next 4 minutes then a constant 99 for 23 seconds. Instead of manually entering this data for every material the user can go to the website and download the software. Also, the user may know they are using a particular substance and there may be a code which would in turn direct the time and temperature control means. For instance, a code could be inputted into an information input/output means such buttons to effectuate an adjustment in the heater means and/or suction means such as to provide optimal vaporization.

The apparatus 10 works on convection, with the temperature controlled by a time and temperature control means which may be affected by a user pressing buttons. By way of example the time and temperature control means, according to a preferred embodiment, may be given a set of directions through the pressing of a left button which may be used to reduce the temperature and the right button may be used to increase the temperature. The temperature may be sensed by temperature sensing means, which is a small diode size sensor. These buttons may also be used to control the time the unit is on. The temperature may be viewed through the use of a LCD display 5 which may be used to display the temperature and time. This may be a digital LCD or LED screen that displays the temperature and time elapsed. The LED light may be used to indicate when the apparatus is on, charging or charged—it may turn a different color corresponding to each state. Buttons 7 and 8 may be used to program the device. By way of example program set button 6 may be used to set the temperature. For example, the temperature and time may be adjusted using button 7 and button 8, then the "program set" button 27 may be depressed in order to set the entered program. Button 8, button 7 and "program set" button 6 will deliver a set of instructions to the time and temperature control means, which will in turn deliver a set of directions to the heater means and the user of the device as the suction means is inhalation. Also, the "program set" button 6 may be used to turn on the heater. The "enter" button 8 is depressed after the "program set" button to activate the program. The air is directed by way of a suction means, and heated through the use of a heater means. The Heating chamber 3 may be inserted into the apparatus 10 and ejected from apparatus. Once the Heating chamber 3 is ejected, a substance may be placed in the source material holder which is contained within the Heating chamber 3 and heated air allowed to flow over the source material holder and the substance contained therein creating a vapor. The apparatus 10 may be programmed to be pre-heated, once an optimal temperature is reached the Heating chamber 3 may be ejected, a substance placed in the source material holder and the Heating chamber 3 inserted back into the apparatus 10 and the materials vaporized.

According to another embodiment, the Heating chamber 3 would have a digitally encoded material holders that would recognize the substance contained therein and direct the time and temperature control means accordingly. By way of example, the disk may sense that the material contained with the disk in Marlboro™ brand tobacco. The optimal vaporization temperature for Marlboro brand tobacco is exactly 122.degree. for the first two minutes, then 100.degree. F. for the next one minute, then 134.degree. F. for the next four minutes, then a constant 99.degree. F. for 23 minutes. The optimal vaporization may also be provided by the information retrieval and delivery means and may be chosen from the group consisting of USB, firewire, ethernet, ilink interface, AN interface, telephone cable interface, parallel interface, fiberoptic, wireless ethernet, and serial interface connected to the apparatus and an information source.

There may also be a mesh materials holder placed in the Heating chamber 3 to contain the substance, while allowing air to flow over the substance. Also, a tablet composed of compressed herbs or other substances molded into a shape which would allow receipt into the source material holder. It should be understood that the tablet may be composed of real drugs, biological drugs, pharmaceutical substances, synthetic or natural substances, hormones and/or insulin. The herbal tablet would have holes in it in order to allow the hot air to pass through it and vaporize the material. Also, oils, resins and other liquids may be used in the device by applying to a sponge material that may be placed in the source material holder or direct application to the substance. Tablets may also be made of a non-active material whose sole use is to be a carrier for liquid that is vaporized in the apparatus 10.

In an alternative embodiment, a window may be used so that a user or a health care professional can monitor the vapor and make a visual ID of it. The air outlet slits vents may be used to cool the heater. The vaporized substance flows through the mouthpiece 1 through the opening 11 in the top 12. The mouthpiece 1 will have a filter 21 at the beginning of the opening 11 where it faces the heating chamber 3. This can be a mesh or fiber filter or any combination thereof.

The vapor created by the apparatus is allowed to exit the device through an opening 11 in the mouthpiece 1. It should be understood that the opening 11 is used by an individual to inhale the vapor. When used by an individual to inhale the vapor through the opening it is desirable to be comfortably hand held with an insulator 2 that wraps around the front of unit casing 4 where the heating chamber 3 is contained.

FIG. 1 depicts the interior of the apparatus according to a preferred embodiment. As shown, the apparatus comprises in combination a power means via a DC Power Input 6 in electrical communication with a heater means 36, a thermocouple for sensing temperature, an information retrieval and delivery means in electrical communication with the power means, a time and temperature control means that adjusts the heat produced by the heater means 36 and length of time heat is produced, information output means in electrical communication with the power means and an LCD display 5 that displays the temperature and time; also a source material holder 22 which is insertable and removable for holding the substance, a mouthpiece 1 and an opening 11. The thermocouple for sensing temperature may be that depicted by temperature sensing means. It should be understood that the temperature sensing means 38 may be on the inside or outside of the receptacle 40. The time and temperature control means produces a variable heat according to the specific substance being volatized in the apparatus. The heat provided by the heater means is preferably between 0.degree. C. and 100.degree. C. and the airflow between 0 and 10 liters/min.

As used and according to a preferred embodiment, the housing is configured and sized to fit in the user's hand during use. The housing, in the preferred embodiment, is ergonomically designed to fit in the user's hand with and insulator 2. The inhaling by the user delivers air to create an air stream which combines with heat from the heating means 36 to provide a convection air stream. An air stream is directed over a heating chamber 3 which includes a cavity for holding a substance, creating a substance vapor air stream and mouthpiece 1 having an opening 11 in communication with the heating chamber 3 receives the substance vapor air stream. The heater is preferably a Ceramic UF Heater.

The apparatus 10 may also release the volatile elements from the opening into the ambient air. Time and temperature control means produces a variable heat according to the specific substance being volatized in the apparatus 10. Also, as discussed in previous embodiments, the information input/output means may be in electrical communication with the time and temperature control means, and power means and allow for adjustment of the temperature, time and airflow. Information may also be manually entered into said information input/output means which in turn electrically communicates with said power means, heater means to adjust the temperature within said apparatus for a specified time. The information retrieval and delivery means may also be a disk contained within said apparatus which automatically senses the nature of the material and provides information to the apparatus such as to provide optimal release of volatile elements of the substance. A mesh materials holder contained within the heating chamber 3 may be used in order to prevent the inhalation of extraneous particles and to contain the substance. The mesh materials holder may also have a substance embedded in it. According to another embodiment, a pre-formed substance with holes formed to be contained within the source material holder.

It should be understood that the foregoing relates to preferred embodiments of the invention and that modifications may be made without departing from the spirit and scope of the invention as set forth in the following claims.

What is claimed is:

1. An apparatus for the vaporization of a substance, said apparatus comprising in combination: a housing, a mouthpiece, a power means for providing electricity contained within said housing; a heater means for providing heat located distally from said mouthpiece; an LCD display; a removable heating chamber used to hold a substance; an air intake means for allowing the intake of air located distally from said heater means and above a proximal end of said mouthpiece; and a fanless suction means for intaking air wherein said fanless suction means originates from said mouthpiece and wherein air is drawn from said air intake means to create an air stream which combines with said heater means to provide a convection air stream.

2. The apparatus as in claim 1 further comprising a receptacle for receiving a vapor that results from the release of volatile elements created by heated air directed from said heater means releasing said volatile elements.

3. The apparatus as in claim 1 further comprising an information retrieval and delivery means for receiving and conveying information in electrical communication with said power means, wherein said information retrieval and delivery means includes a disk within said removable heating chamber contained within said apparatus which automatically senses the nature of said substance and provides information to said apparatus such as to provide optimal release of volatile elements of said substance; and an opening for allowing release of vapor.

4. The apparatus as in claim 1 further comprising a time and temperature control means for determining passage of time and regulating temperature wherein said time and temperature control means produces a variable heat according to the specific substance being volatized in said apparatus.

5. The apparatus as in claim 3 further comprising an interface for said information retrieval and delivery means chosen from the group consisting of a USB interface, firewire, ethernet, fiberoptic, wireless Ethernet, ilink interface, AN interface, telephone cable interface, parallel interface, and serial interface connected to said apparatus and an information source.

6. The apparatus as in claim 1, wherein said fanless suction means creates an airflow between 0 and 10 Liters/min.

7. The apparatus as in claim 1 further comprising an insulator connected to said housing.

8. The apparatus as in claim 2 further comprising at least one viewing means for viewing said vapor within the receptacle.

9. The apparatus as in claim 1 wherein said removable heating chamber includes a cavity for holding a pre-formed substance with holes.

10. The apparatus as in claim 1 wherein said housing is configured and sized to fit in a user's hand during use.

11. The apparatus as in claim 10 wherein said housing is ergonomically designed.

12. An apparatus that allows for inhalation of active elements of a substance comprising;
  a housing configured and sized to fit in a user's hand during use;
  a power means for supplying power to a heating means for providing heat, information retrieval and delivery means for receiving and conveying information, time and temperature control means for determining passage of time and regulating temperature, information input/output means, display means for displaying information, an air intake means for allowing the intake of air located distally from said heating means, and a fanless suction means for intaking air located distally from said heating means and wherein a proximal end of said fanless suction means is located below said air intake means;

at least one viewing means for viewing vapor, contained therein;

wherein said fanless suction means draws an air stream from said air intake means which combines with heat from said heating means to provide a convection air stream; wherein said convection air stream is directed over a source material holder which includes a cavity for holding a substance, creating a substance vapor air stream; and said housing having therein a receptacle having at least one opening in communication with said source material holder for receiving said substance vapor air stream and having a DC power source contained in said housing.

13. The apparatus as in claim 10 wherein said housing is ergonomically designed.

* * * * *